(12) United States Patent
Bert

(10) Patent No.: US 11,226,381 B2
(45) Date of Patent: Jan. 18, 2022

(54) COMPACT DIAMOND NV CENTER IMAGER

(71) Applicant: Palo Alto Research Center Incorporated, Palo Alto, CA (US)

(72) Inventor: Julie A. Bert, East Palo Alto, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 0 days.

(21) Appl. No.: 16/665,375

(22) Filed: Oct. 28, 2019

(65) Prior Publication Data

US 2021/0123988 A1    Apr. 29, 2021

(51) Int. Cl.
*G01R 33/032* (2006.01)
*A61B 5/055* (2006.01)

(52) U.S. Cl.
CPC ............ *G01R 33/032* (2013.01); *A61B 5/055* (2013.01)

(58) Field of Classification Search
None
See application file for complete search history.

(56) References Cited

U.S. PATENT DOCUMENTS

| | | | | |
|---|---|---|---|---|
| 2008/0096308 | A1* | 4/2008 | Santori | G02B 6/122 438/105 |
| 2010/0271016 | A1* | 10/2010 | Barclay | G01R 33/032 324/244.1 |
| 2014/0166904 | A1* | 6/2014 | Walsworth | G01N 21/645 250/459.1 |
| 2016/0146904 | A1* | 5/2016 | Stetson, Jr. | G01R 35/005 324/202 |
| 2016/0313408 | A1* | 10/2016 | Hatano | G01R 33/032 |
| 2017/0212185 | A1* | 7/2017 | Hahn | G01R 33/032 |
| 2018/0202952 | A1* | 7/2018 | Lutz | G01N 24/08 |

OTHER PUBLICATIONS

D. Le Sage, "Optical Magnetic Imaging of Living Cells", Nature, Apr. 25, 2013.
Chipaux, "Nitrogen Vacancies (NV) Centers in Diamond for magnetic Sensors and Quantum Sensing",Proceeding of SPIE, 2015, San Francisco, California, United States.
A. Gruber, A. Drabenstedt, C. Tietz, L. Fleury, J. Wrachtrup, and C. v. Borczyskowski, "Scanning Confocal Optical Microscopy and Magnetic Resonance on Single Defect Centers", Science, Jun. 1997.
S. Steinert, "High sensitivity magnetic imaging using an array of spins in diamond", Review of Scientific Instruments, 81, 043705 (2010).
M. Chipaux,"Wide bandwidth instantaneous radio frequency spectrum analyzer based on nitrogen vacancy centers in diamond", Applied Physics Letters 107, 233502 (2015).
M. Chipaux, "Magnetic imaging with an ensemble of nitrogen-vacancy centers in diamond", The European Physical Journal D, (2015).

* cited by examiner

*Primary Examiner* — Jas A Sanghera
(74) *Attorney, Agent, or Firm* — Fay Sharpe, LLP

(57) ABSTRACT

The following relates generally to a magnetic imaging sensor configured to capture vector magnetometry data. One disclosed aspect involves: using a green pumping laser to excite nitrogen vacancy (NV) centers of a diamond crystal; and, through a filter stacked between the diamond crystal and a pixilated image sensor, passing red light caused by the excitation to the pixilated image sensor.

20 Claims, 4 Drawing Sheets

COMPACT DIAMOND NV CENTER IMAGER

BACKGROUND

The present application relates generally to a magnetic imaging sensor configured to capture vector magnetometry data.

BRIEF DESCRIPTION

In accordance with one aspect of the present application, there is a system for measuring a local magnetic field, including: a green pumping laser configured to excite nitrogen vacancy (NV) centers of a diamond crystal; a radio frequency (RF) coil configured to shift energy of a photoluminescence signal; and a magnet configured to break a degeneracy of the NV centers; and a filter configured to pass red light caused by the excitation to an image sensor thereby creating the photoluminescence signal, wherein the filter is stacked between the diamond crystal and the image sensor to create a compact device.

In the system as described in the preceding paragraph, the image sensor may be pixelated to provide a spatially resolved magnetic field image. The system may further include a reflector stacked on a surface of the diamond crystal opposite of a surface of the diamond crystal stacked on the filter. In some embodiments, the reflector is connected to the surface of the diamond crystal opposite of the surface of the diamond crystal connected to the filter by deposition of aluminum reflective metallic mirror on the diamond crystal. In some embodiments, the reflector is a red light reflector. In some embodiments, the filter and the image sensor are connected with an adhesive that is transparent for red light. In some embodiments, the filter and the image sensor are connected with an adhesive that has an index of refraction that is larger than one and less than an index of refraction of the diamond crystal. In some embodiments, the filter and the diamond crystal are glued together with an adhesive that blocks green laser light. In some embodiments, the filter is a long pass filter. In some embodiments, the filter is a band pass filter. In some embodiments, the filter is an absorption filter. In some embodiments, the filter is an interference filter. In some embodiments, the system further includes: a radio frequency (RF) coil stacked on a mirror stacked on the diamond crystal; wherein the RF coil is configured to drive electron population transitions and readout a local projection of a magnetic field along a center crystallographic axis of the NV center defects.

In another disclosed aspect, there is a device for vector magnetic image sensing, including: a green pumping laser configured to excite nitrogen vacancy (NV) centers of a diamond crystal; a filter configured to filter a red light caused by the excitation through to a image sensor thereby creating a photoluminescence signal, wherein the filter is stacked between the diamond crystal and the image sensor; a radio frequency (RF) coil configured to apply radiation to the diamond crystal; a magnet configured to break a degeneracy of the NV centers; at least one processor; and at least one memory including computer program code; the at least one memory and the computer program code configured to, with the at least one processor, cause the device at least to: measure the local magnetic field by measuring a frequency of a radiation where the photoluminescence signal drops.

In another disclosed aspect, there is a method for measuring a local magnetic field, including: using a green pumping laser to excite nitrogen vacancy (NV) centers of a diamond crystal; sweeping the frequency of a radio frequency (RF) coil to modulate a photoluminescent signal; and, through a filter stacked between the diamond crystal and an image sensor, passing red light caused by the excitation to the image sensor measuring the photoluminescent signal.

DETAILED DESCRIPTION

Some embodiments describe a compact magnetic imaging sensor capable of capturing vector magnetometry data in a small portable package. This utilizes nitrogen vacancy (NV) center defects in diamond which have the potential to have the highest sensitivity and highest spatial resolution of all magnetic sensors. Some embodiments relate to a technique to develop a portable package to replace a large benchtop system.

Figure 1A:
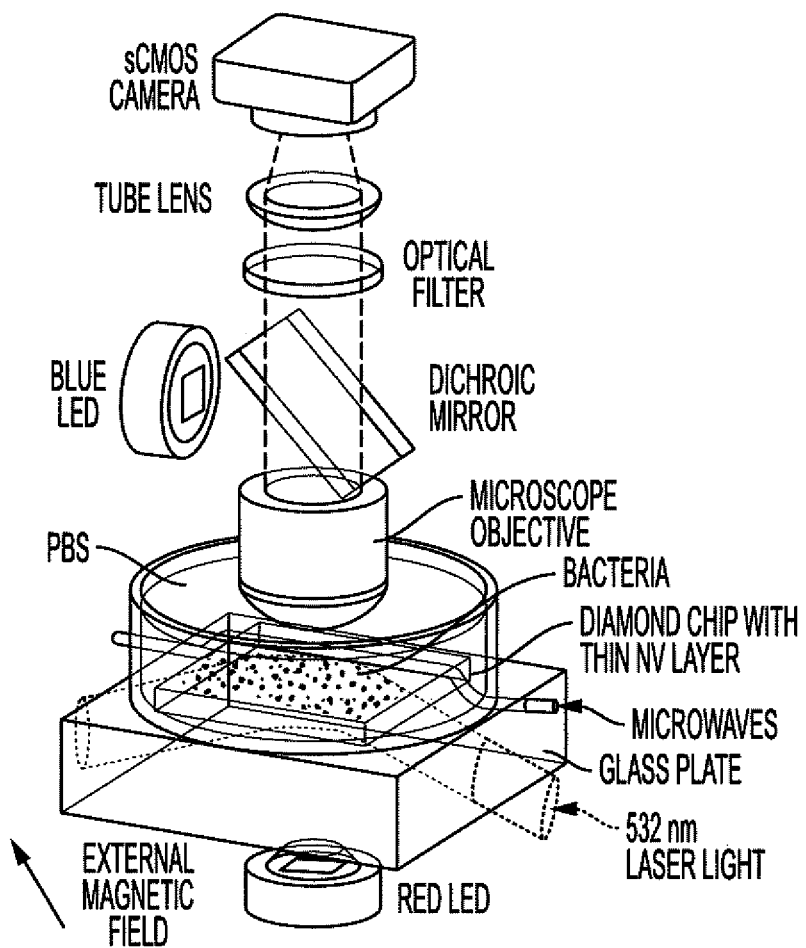
FIG. 1A illustrates a previously known large benchtop NV center magnetic microscope.

Some embodiments relate to a compact magnetic imaging sensor capable of capturing vector magnetometry data in a small portable package. A large benchtop NV center magnetic microscope is known in the art and shown in FIG. 1A [D. Le Sage, Nature (2013)].

Figure 2:
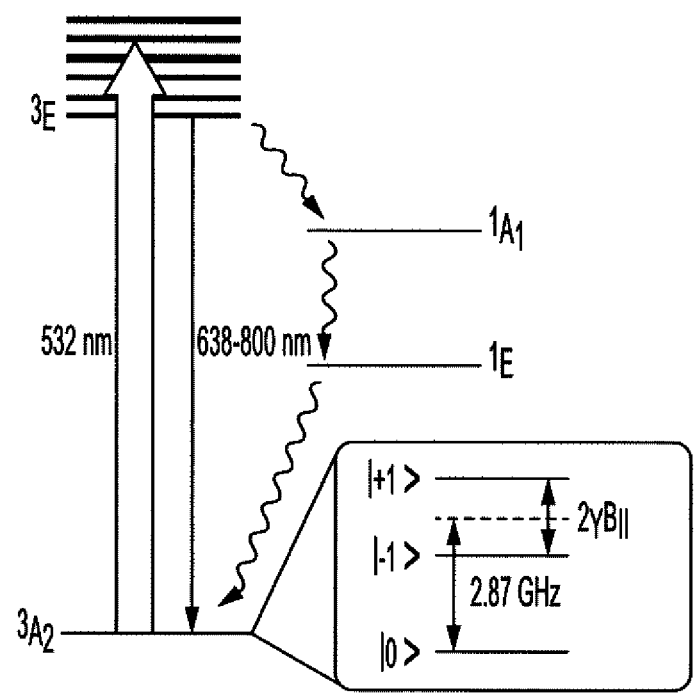
FIG. 2 illustrates an operational principle of the NV-diamond magnetometry.

A nitrogen vacancy (NV) center is an atomic-scale point defect in a diamond crystal lattice. A nitrogen atom substitutes for a carbon atom in the diamond lattice and forms a nearest neighbor pair with a lattice vacancy. In some cases, the NV center attracts an additional electron and it and an unbound electron from the vacancy form a spin 1 pair with quantized energy levels as shown in the example of FIG. 2. The photoluminescence intensity of the NV is proportional to the relative population of the spin 1 and spin 0 energy levels because the excitation is spin conserving and the spin 1 first excited state has a non-radiative decay path. Microwave radiation at an energy equal to the splitting of the spin 1 and spin 0 ground states can change the population of each of these states driving spin 0 electrons into the spin 1 state. An applied magnetic field splits the degeneracy in the spin +1 and spin −1 states which shifts the energy splitting between the spin 0 and spin −1 states. Consequently, by exciting the NV with laser light (e.g. green laser light) and concurrently sweeping the applied microwave frequency, the local magnetic field can be measured at the NV directly from the frequency value where the photoluminescence signal drops. In a luminescence vs microwave frequency graph, there will be two "dips" for each NV center, which correspond to the energy between the spin −1 and spin 0 states and the spin 1 and spin 0 states. In addition, regarding FIG. 2, it should be understood that γ represents a physical constant. It should further be understood that the frequency depends on the magnetic field parallel to the defect axis, represented by $B_{\parallel}$.

An ensemble of NV centers can be implanted in a diamond crystal forming a 2D area of NV center defects just below the surface. The diamond crystal lattice presents a four-fold degeneracy in the orientation of the NV center. Each orientation is sensitive to the projection of the local magnetic field onto the defect axis. Consequently, an NV center ensemble can be used to generate a vector reconstruction of the local magnetic field. To make the ensemble measurement, the NV centers are excited in some embodiments by green laser light while the red photoluminescent output is imaged onto a pixelated detector to measure the local magnetic field. Large, benchtop NV center magnetic microscopes are known in the art. In all cases, the imager set-up uses an inverted microscope, upright microscope, or free space optics coupled to a microscope objective to image the NV centers. These set-ups work well for imaging magnetic fields in microscopic samples but have not been adapted to handheld or portable imaging applications.

Figure 1B:
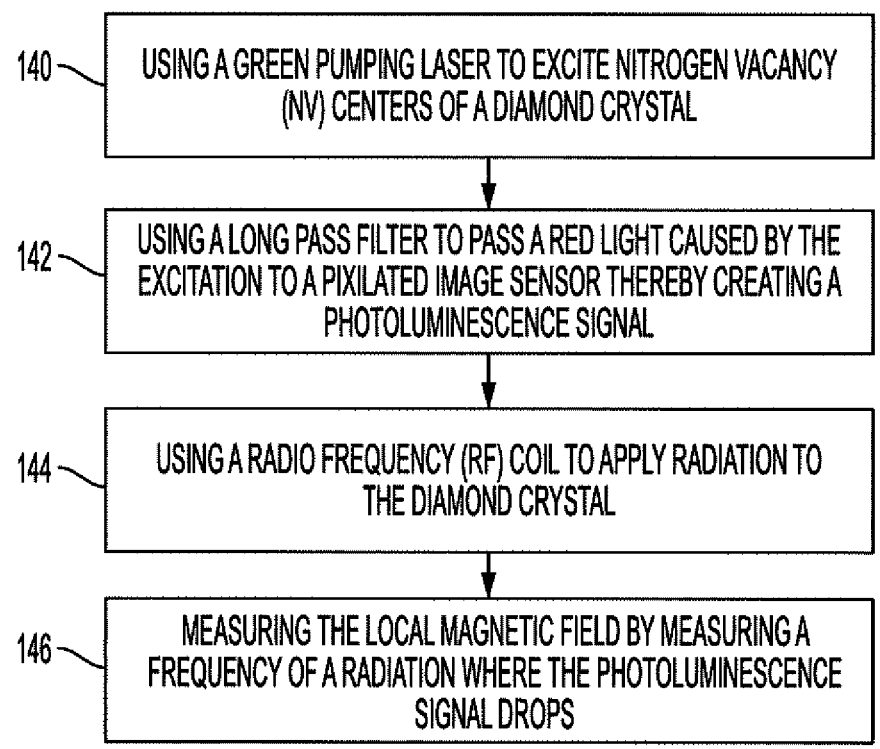
FIG. 1B illustrates a method of magnetic imaging.

FIG. 1B illustrates a method of magnetic imaging. With reference thereto, step 140 shows using a green pumping laser to excite NV centers of a diamond crystal thereby creating a photoluminescence signal. Step 142 shows using a long pass filter to pass a red light caused by the excitation to a pixelated image sensor thereby detecting and imaging the photoluminescence signal. Step 144 shows using a RF coil to apply radiation to the diamond crystal. Step 146 shows measuring the local magnetic field by sweeping the applied frequency of the RF coil and measuring a frequency of a radiation where the photoluminescence signal drops.

Figure 1C:
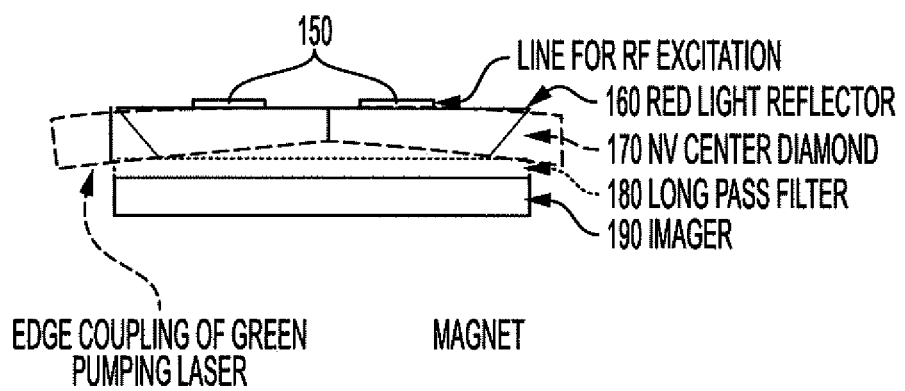
FIG. 1C shows a compact magnetic imager in accordance with one embodiment as described herein.

FIG. 1C shows a compact magnetic imager in accordance with one embodiment. As illustrated in FIG. 1C, a diamond crystal with implanted NV center defects and optical long pass filter is stacked directly on a pixelated image sensor. Green laser light is coupled in from the side of the diamond and totally internally reflected within the diamond to excite the NV center bound state electrons while minimizing the green background in the photoluminescence measurement. NV centers emit light isotopically in all directions. A red light reflector is included on the diamond surface opposite the long pass filter to reflect light back towards the image sensor and double the collection efficiency. This reflector can optionally be omitted if spatial resolution is more critical that signal sensitivity. An integrated radio frequency (RF) coil 150 is included on top of the mirror diamond surface to drive the electron population transitions and readout the local projection of the magnetic field along the NV center's crystallographic axis. As the frequency is swept, a series of pairs of dips each corresponding to a NV center projection can be seen. In addition, a magnet (either permanent or electromagnet) is included to break the degeneracy of the NV ensemble projections and spectrally separate the dips in the photoluminescence vs. RF frequency plot. Because the magnet may suitably be placed in different locations, a specific location of the magnet is not shown in FIG. 1C. The device stack up includes: optional top red light reflector 160, diamond crystal 170, long pass filter 180 and the image sensor 190. In some embodiments, any or all of the components are connected with no gap either by direct deposition (e.g., sputtering an aluminum mirror on the top surface of the diamond substrate). In other embodiments, any or all of the components are coupled with a high index adhesive that is transparent for red light. If an adhesive that is transparent for red light and opaque for other colors of light is used, this could combine the purpose of the long pass filter and the adhesive, and thus eliminate the need for using a long pass filter which would eliminate some thickness and thereby improve resolution. Matching the index of the adhesive material to diamond's index (n=2.4) will improve the spatial resolution and light collection efficiency. However, it is unlikely that a red transparent adhesive is available with such a large index. The highest possible index adhesive that still meets the transparency requirements should be used. In one example, an optically clear adhesive with an index of about 1.4 is used.

It should be understood that if an adhesive is not used, there might be an air gap (e.g. where the adhesive would otherwise be between the various layers of diamond, filter and image sensor) along at least a portion of contacting layers. In some embodiments, between layers where no adhesive is used, there is no purposely created space but air gap(s) still exist along certain portions of the edges. In some aspects, the airgap is a nuisance because its presence can create some diffusion in the light signal that decreases spatial resolution. Thus, in some exemplarily embodiments, there is no airgap. In some embodiments, the long pass filter is pressed to the imager (instead of gluing it), in which case a small airgap may be unavoidable.

There are many options for the components described above, and the examples given are not meant to limit the design variations. For example, various long pass filters or other filters may be used. In this regard, a purpose of the filter is to block the (532 nm) green laser light. For example, in some embodiments, the filter passes 639-800 nm light and blocks 532 nm light (e.g. the filter may be a bandpass filter). In another example, the filter may be a long pass filter. In one aspect, the filter can be an absorption filter or an interference filter. The filter could be directly deposited onto the diamond crystal or glued to the diamond crystal with a high index adhesive that is also transparent in certain wavelength ranges (e.g. 639-800 nm) such that the green laser light is blocked. Similarly, the top red light reflector could be done with a broad band reflector (mirror) or low frequency reflector that just reflects light in a particular band such as the 639-800 nm band. The reflector can be deposited directly on the diamond or glued to the diamond with a high index adhesive. The image sensor can be any light to charge converter and can be pixelated or not. Examples include complementary metal-oxide-semiconductor (CMOS) imagers, charge-coupled device (CCD) imagers, and large area thin film transistor/photodiode imagers.

In some embodiments of this compact system, the spatial resolution will be limited by the larger of the thickness of the optical stack (diamond crystal and long pass filter) or the imager pixel. The diamond crystal minimum thickness is set by the mechanical stability of the diamond and the thickness needed to get good coupling for the green excitation laser. Diamond crystal thickness of 250 um which have been polished for edge coupling of the totally internally reflected laser light have been reported. [Chipaux, The European Physical Journal D 2015]. If an imager with pixels smaller than the optical stack thickness is selected, pixel binning up to the size of the optical stack can be done to increase the signal size with no loss of resolution. In some embodiments, the thickness of the diamond is the same as the pixel size of the image sensor.

The overall imaging area will also be limited by the size of the diamond crystal. NV diamond crystals as large as 4 mm×4 mm have been demonstrated in the art, but larger crystals may be possible. The size of the available diamond crystal will impact the choice of image sensor used in the stack. If diamond substrate sizes remain small, a CMOS imager will likely the best choice. A state of the art 4K 2.8 um pixel CMOS sensor is 11 mm×11 mm. However, NV diamond crystals could also be tiled across the surface of an imager and connected with a high index adhesive to cover a large area. In this case, an a-Si thin-film-transistor (TFT) imager could be selected as the image sensor to create a large area, portable, high sensitivity magnetic imager with high spatial resolution.

In some embodiments, the NV centers are near the top surface of the diamond 170 (e.g. near the red light reflector 160). In one example, the NV centers are 5 nm-40 nm from the top surface of the diamond 170. The precise distance depends on the energy of implementation. In other embodiments, the NV centers may be near a bottom surface of the diamond 170 (e.g. near the filter 180).

Moreover, NV diamond magnetometers can operate a room temperature (unlike superconducting quantum interference device (SQUIDs)), can measure the vector projections of the magnetic field (unlike optically-pumped magnetometers (OPMs)), and, in an ensemble configuration, they provide natural 2D imaging unlike all the other sensing technologies which are essentially OD point like sensors.

Some embodiments described herein add portability to the other benefits of the NV magnetometer imaging system and enable the image sensor to be used in field environments for non-destructive testing or in clinical environments for medical imaging. For example, some embodiments can be used to measure neuron activity (e.g., neurons firing) by use of a small portable device. In some embodiments, the small portable device is 1 inch by 1 inch by 1 inch, and uses three cables (a digital cable for the camera, a RF cable for the RF coil, and a fiber cable for the laser). The small portable device can easily be strapped to a patient at any suitable location on the patient. It should be understood that it is the contact imaging (e.g. the diamond crystal in direct contact with the adhesive in direct contact with the image sensor) as described herein that allows for this advantageous portability.

It will be further appreciated that the techniques disclosed herein may be embodied by a non-transitory storage medium storing instructions readable and executable by an electronic data processing device to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A system for measuring a local magnetic field, comprising:
    a diamond crystal containing nitrogen vacancy (NV) centers;
    a green pumping light source configured to excite the NV centers of the diamond crystal;
    a radio frequency (RF) coil configured to shift energy of a photoluminescence signal;
    a magnet configured to break a degeneracy of the NV centers;
    a filter configured to pass red light caused by the excitation to an image sensor thereby creating the photoluminescence signal, wherein the filter is stacked between the diamond crystal and the image sensor; and
    a reflector stacked on a surface of the diamond crystal opposite of a surface of the diamond crystal stacked on the filter.

2. The system of claim 1, wherein the image sensor is pixelated to provide a spatially resolved magnetic field image.

3. The system of claim 1, wherein the reflector is connected to the surface of the diamond crystal opposite of the surface of the diamond crystal connected to the filter by deposition of a reflective material on the diamond crystal.

4. The system of claim 1, wherein the reflector is a red light reflector.

5. The system of claim 1, wherein the filter and the image sensor are connected with an adhesive that is transparent for red light.

6. The system of claim 1, wherein the filter and the image sensor are connected with an adhesive that has an index of refraction that is larger than one and less than an index of refraction of the diamond crystal.

7. The system of claim 1, wherein the filter and the diamond crystal are glued together with an adhesive that blocks green light.

8. The system of claim 1, wherein the filter is one of a long pass filter, a band pass filter, an absorption filter and an interference filter.

9. The system of claim 1, wherein:
    the RF coil is stacked on the reflector stacked on the diamond crystal; and
    the RF coil is configured to drive electron population transitions and readout a local projection of a magnetic field along a center crystallographic axis of the NV center.

10. A system for measuring a local magnetic field, comprising:
    a pixelated image sensor;
    a plurality of diamond crystals attached across a face of the image sensor;
    a green pumping light source configured to excite nitrogen vacancy (NV) centers of the plurality of diamond crystals, the green pumping light source and plurality of diamond crystals being arranged such that a green light of the green pumping light source is laterally transmitted parallel to a plane of the image sensor to neighboring crystals and that a red light emission from the excited NV centers is totally internally reflected within a single crystal and directed to the image sensor, to make a spatially resolved large area magnetic imaging sensor with a spatial resolution defined by lateral dimensions of the diamond crystals, said lateral dimensions being parallel to the face of the image sensor;
    a radio frequency (RF) coil configured to shift energy of a photoluminescence signal;
    a magnet configured to break a degeneracy of the NV centers; and
    a filter configured to pass red light caused by the NV excitation to the image sensor thereby creating the photoluminescence signal, wherein the filter is stacked between the plurality of diamond crystals and the image sensor.

11. The system of claim 10, further comprising:
    a reflector stacked on a side of the diamond crystals opposite of a side of the diamond crystals on which the filter is stacked.

12. The system of claim 11, wherein the reflector is formed by deposition of a reflective material on the diamond crystals.

13. The system of claim 11, wherein the reflector is a red light reflector.

14. The system of claim 11, wherein the filter and the image sensor are connected with an adhesive that is transparent for red light.

15. The system of claim 10, wherein the plurality of diamond crystals are laterally glued together with an adhesive that blocks red light and transmits green light.

16. The system of claim 10, wherein the filter and the image sensor are connected with an adhesive that has an index of refraction that is larger than one and less than an index of refraction of the diamond crystals.

17. The system of claim 10, wherein the filter and the diamond crystals are glued together with an adhesive that blocks green light.

18. The system of claim 10, wherein the filter is one of a long pass filter, a band pass filter, an absorption filter and an interference filter.

19. A method for measuring a local magnetic field, comprising:
   using green light from a light source to excite nitrogen vacancy (NV) centers of a plurality of diamond crystals laterally arranged across a face of a pixelated image sensor;
   sweeping a frequency of a radio frequency (RF) coil to modulate a photoluminescent signal;
   measuring the photoluminescent signal; and
   passing red light caused by the excitation of the NV centers to the image sensor through a filter stacked between the diamond crystals and the image sensor;
   wherein the light source and plurality of diamond crystals are arranged such that the green light from the light source is laterally transmitted between neighboring crystals while the red light caused by the excitation of NV centers is internally reflected laterally within each single crystal and directed out of each single crystal toward the image sensor, thereby creating a spatial resolution for said measuring defined by lateral dimensions of the diamond crystals, said lateral dimensions being parallel to the face of the image sensor.

20. A method for measuring a local magnetic field, comprising:
   exciting nitrogen vacancy (NV) centers of a diamond crystal with green light from a light source;
   shifting an energy of a photoluminescence signal with a radio frequency (RF) coil;
   breaking a degeneracy of the NV centers with a magnet;
   passing red light caused by exciting the NV centers through a filter to an image sensor thereby creating the photoluminescence signal, wherein the filter is stacked between the diamond crystal and the image sensor; and
   reflecting red light caused by exciting the NV centers from a reflector stacked on a first side of the diamond crystal opposite of a second side of the diamond crystal on which the filter is stacked.

* * * * *